United States Patent [19]
Roussy et al.

[11] Patent Number: 5,411,649
[45] Date of Patent: May 2, 1995

[54] CATALYTIC PROCESS FOR CONTROLLED OXIDATION OF METHANE USING MICROWAVES FOR THE SYNTHESIS OF ETHANE AND ETHYLENE AND CATALYSTS USED IN THIS PROCESS

[75] Inventors: Georges Roussy, Laxou; Christophe Marchand, Thomery; Jean-Marie Thiebaut, Heillecourt; Mina Souiri, Tunisie; Alain Kiennemann, Illkirch; Corinne Petit, Strasbourg; Gilbert Maire, Haguenau, all of France

[73] Assignee: Electricite De France, Service National, France

[21] Appl. No.: 131,428

[22] Filed: Oct. 4, 1993

[30] Foreign Application Priority Data

Oct. 2, 1992 [FR] France .................. 92 11676

[51] Int. Cl.$^6$ ................................. C01B 3/00
[52] U.S. Cl. ............................ 204/157.43; 204/157.6; 204/168; 502/5
[58] Field of Search ................ 204/157.43, 157.6, 168; 502/5

[56] References Cited

U.S. PATENT DOCUMENTS

| 4,574,038 | 8/1993 | Wan ...................... 204/162 R |
| 5,205,912 | 4/1993 | Murphy .................. 204/157.43 |
| 5,266,175 | 11/1993 | Murphy ................ 204/157.43 |
| 5,277,773 | 1/1994 | Murphy ................ 204/157.43 |

FOREIGN PATENT DOCUMENTS

| 0283379 | 3/1988 | European Pat. Off. . |
| 0320301 | 12/1988 | European Pat. Off. . |
| 0335130 | 3/1989 | European Pat. Off. . |
| 0492695 | 12/1991 | European Pat. Off. . |
| 2227249 | 1/1990 | United Kingdom . |
| 9202448 | 2/1992 | WIPO . |

OTHER PUBLICATIONS

"The Oxidative Coupling of Methane over Alkali, Alkaline Earth, and Earth Oxides" of J. M. Deboy et al., 1988.
Chemical Abstracts, vol. 117, No. 3, Jul. 20, 1992–abstract No. 25918c.
"Installation D'Irradiation Microonde des Catalyseurs Dielectriques et d'Etude des Reactions" of Thiebaut et al., 1988.

Primary Examiner—John Niebling
Assistant Examiner—C. Delacroix-Muirheid
Attorney, Agent, or Firm—Larson and Taylor

[57] ABSTRACT

Catalytic process for controlled oxidation of methane using microwaves, characterized in that it makes use of a catalyst exhibiting in its structure electrical charge defects and geometric deformations enabling it to absorb electromagnetic energy, or microwaves, under the effect of an electromagnetic field.

9 Claims, 2 Drawing Sheets

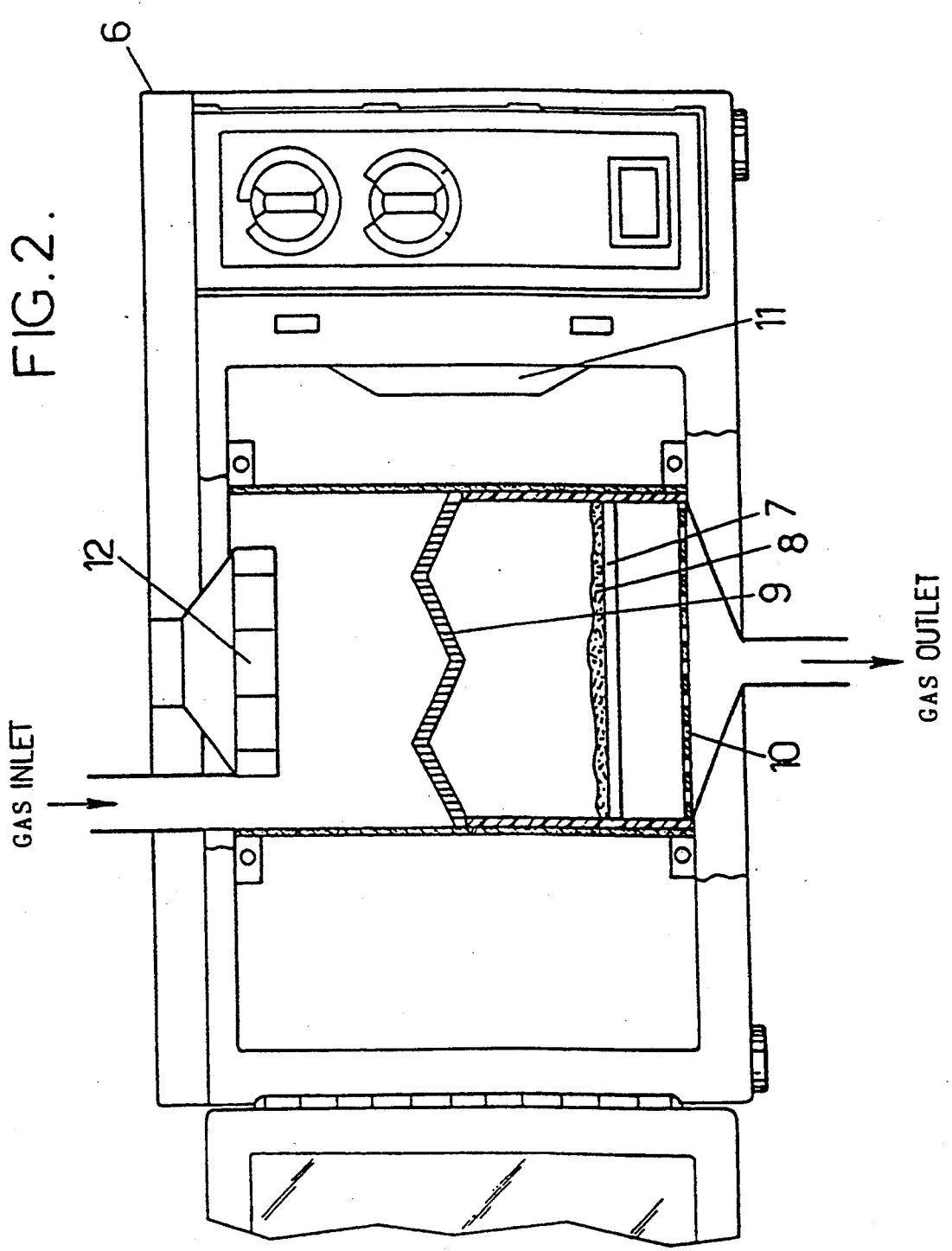

CATALYTIC PROCESS FOR CONTROLLED OXIDATION OF METHANE USING MICROWAVES FOR THE SYNTHESIS OF ETHANE AND ETHYLENE AND CATALYSTS USED IN THIS PROCESS

The invention relates to a catalytic process for controlled oxidation of methane using microwaves for the synthesis of ethane and ethylene.

BACKGROUND OF THE INVENTION

It is known to react methane and hydrogen in a plasma to synthesize $C_2$ hydrocarbons (ethane and ethylene) directly. The plasma may be obtained in a microwave oven and may be initiated by metals such as Ni, Fe or Co, finely divided, and by mixtures of these metals, also highly divided.

The disadvantage of this process is that, on the one hand, much energy is needed to maintain the plasma and, on the other hand, the efficiency of obtaining $C_2$ molecules is low, despite the technical improvements which it has been possible to propose (as in U.S. Pat. No. 4,574,038).

Another process consists in partially and catalytically oxidizing methane to synthesize ethane according to the reaction (1):

$$2CH_4 + \tfrac{1}{2}O_2 \rightarrow C_2H_6 + H_2O$$

and then ethylene according to the reaction (2):

$$C_2H_6 + \tfrac{1}{2}O_2 \rightarrow C_2H_4 + H_2O.$$

The disadvantage of this method lies in the fact that the oxidation is difficult to restrict to the above-mentioned products which are formed and that it also gives rise to carbon monoxide or carbon dioxide according to the reaction (3):

$$CH_4 + (1+x/2)O_2 \rightarrow CO_x + 2\,H_2O$$

with $x=1$ or $x=2$.

Ethane and ethylene can also be oxidized to $CO_x$ as soon as they are produced during reactions (1) and (2). Consequently, this oxidation restricts the efficiency of these reactions, which take place on catalysts such as the oxides: $La_2O_3$, $Sm_2O_3$, $NaPbO$, $MgO$ and $BaO$ at a temperature of at least 600° C. and in most cases in the gaseous phase.

Until now, and irrespective of the methane oxidation process employed, it has not been possible to obtain sufficient yields with high selectivities for the reactions used. At present the yield is at a ceiling of 16% and the selectivity never exceeds 80%. The latter is high only in the case of low degrees of progress of the reactions and, whatever the catalysts employed, it falls when an attempt is made to increase the degree of progress of the reaction by choosing optimum experimental conditions of temperature and pressure.

The yield is defined as being the ratio of the number of molecules of methane ($CH_4$) necessary to form the product (that is to say ethane and ethylene or $C_2$ molecules) to the number of molecules of $CH_4$ entering the plant.

Selectivity (S) means the total selectivity for the product, defined as being the ratio of the number of molecules of $CH_4$ converted into $C_2$ molecules to the total number of converted $CH_4$ molecules.

The degree of progress of the reaction, also called degree of conversion of methane, measures the total usage of methane. It is defined as being the ratio of the number of converted $CH_4$ molecules to the number of $CH_4$ molecules entering the plant.

These measurements can be made by chromatography.

It is recalled that the controlled catalytic oxidation of methane is a complex reaction which takes place in a number of stages:
- adsorption of the methane molecules on the catalytic sites of the solid catalyst,
- conversion of the methane molecules into $CH_3$ radicals in contact with the $O^-$ ions of the solid, to give OH groups, according to the reaction:

$$CH_3(gas) + O^-(surface) \rightarrow CH_3 + OH\ (surface),$$

- combination of the $CH_3$ radicals to give ethane according to the reaction:

$$2\,CH_3 \rightarrow C_2H_6$$

with elimination of the OH groups at the surface of the catalyst in the form of water, which creates gaps bridged by the absorption of oxygen,
- controlled oxidation of ethane to give ethylene according to the reaction:

$$C_2H_6 + \tfrac{1}{2}O_2 \rightarrow C_2H_4 + H_2O$$

Simultaneously, as a result of the presence of oxygen, methane, ethane and ethylene can be partially oxidized, according to the following reaction scheme:

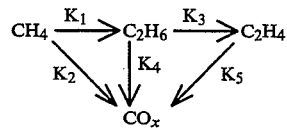

with $x=1$ or $x=2$, each of the reactions shown diagrammatically above taking place individually at its own reaction rate $K_i$, calculated according to the Arrhenius law:

$$K_i = k_i \exp-(E_i/RT)$$

with $k_i$ = rate coefficient
$E_i$ = activation energy
R = constant for perfect gases
T = absolute temperature.

The objective of the invention is to remedy the disadvantages of the prior art and especially to propose new catalysts making it possible to promote the reaction mechanisms resulting in the formation of ethane and ethylene, while reducing those resulting in the formation of CO and $CO_2$.

GENERAL DESCRIPTION OF THE INVENTION

Thus, the inventors have the credit of having found that, surprisingly and unexpectedly, it is possible to produce ethane and ethylene in an overall yield as high as 14.8% with a selectivity of 98%, that is to say with a degree of progress of the reaction of 15.1%, by using particular catalysts to implement a catalytic process for controlled oxidation of methane using microwaves.

These results are obtained by virtue of the use of solid catalysts exhibiting in their structure electrical charge defects and geometric deformations enabling them to absorb electromagnetic energy, or microwaves, under the effect of an electromagnetic field.

Microwaves are intended to mean waves of frequencies corresponding to the bands authorized for Industrial, Scientific and Medical (I.S.M) applications. Among these authorized bands, the catalyst in accordance with the invention is preferably subjected to a frequency chosen from: $13560 \pm 17$ kHz, $27120 \pm 70$ kHz, $433.92 \pm 0.80$ MHz, $915 \pm 15$ MHz, $2450 \pm 50$ MHz and $5800 \pm 75$ MHz.

The catalysts in accordance with the invention are rare-earth oxides or rare-earth alkali metal mixed oxides, optionally doped with at least one alkali metal and/or alkaline-earth metal.

A doped catalyst is intended to mean a catalyst in which at least one constituent rare-earth metal atom has been substituted by an alkali metal or alkaline-earth metal atom of similar size but of different electrical valency.

This substitution is preferably effected with an oxide of the said alkali or alkaline-earth metal, previously dissolved in a preparation.

Such a doping produces a distortion of the initial lattice of the solid catalyst, resulting in electrical charge defects and geometric deformations in this lattice.

However, among the catalysts in accordance with the invention, some are not doped because they exhibit the abovementioned distortion naturally.

This distortion is at the source of a particular distribution of the electrical charges in the catalyst. Whether positive or negative, these electrical charges bind to the surface of the catalyst the free $O^-$ or $O_2^-$ ions in contact with which the methane molecules are converted into $.CH_3$ radicals.

Without wishing to be bound by theory, it is thought that the electromagnetic field selectively activates the free electrical charges present in or at the surface of the solid catalyst, that because of this, and according to the catalytic process for controlled oxidation of methane using microwaves in accordance with the invention, the combinations of electrical charges and oxygen ions are vibrated and excited, this excitation dissipating energy and, as a result, the catalyst absorbing electromagnetic energy. Consequently, the abovementioned conversion reaction is considerably promoted under the action of the microwaves. Everything takes place as if the electromagnetic field were capable of raising the catalytic sites, at which the oxygen and methane molecules are adsorbed, to a temperature which is higher, or even much higher, than the temperature of the solid surrounding the actual catalytic site.

In addition, when the solid catalyst in accordance with the invention is heated by microwaves, it is cooled by the circulating gaseous reactants. In fact, if the thickness of the catalyst layer through which the gases pass is small, the temperature of the gases which leave is much lower than that of the catalyst. Now, the degradation and oxidation reactions of ethane and ethylene (marked 4 and 5 in the reaction scheme above) take place, in most cases, in the gas phase at a temperature of at least 600° C. Therefore, in the case of the catalyst in accordance with the invention, which is heated by microwaves, these reactions are much less extensive and take place at rates which are much lower than in a conventional oven, since the temperature is from 100° to 200° C. lower than that corresponding to conventional heating.

BRIEF DESCRIPTION OF THE DRAWINGS

By way of indication and without the invention being limited thereby:

FIG. 2 shows a pilot version of a plant employing a household microwave oven for the controlled oxidation of methane on the catalysts in accordance with the invention.

DESCRIPTION OF PREFERRED EMBODIMENTS

Figure 1:
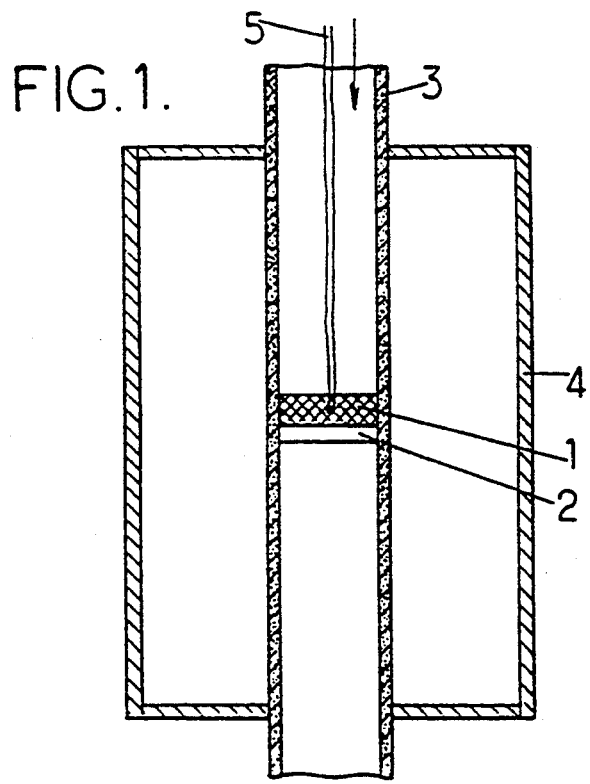
FIG. 1 shows a laboratory microwave applicator enabling the performance of the catalysts in accordance with the/invention to be evaluated.

The method of using the microwave applicator shown in FIG. 1 is as follows:

One $cm^3$ of the catalyst 1 in accordance with the invention is placed on a sinter 2, in a silica tube 3 itself placed in a waveguide 4 (RG 112/U standard guide) which has a section of $8.6 \times 4.3$ cm, the tube being cylindrical with a diameter of 1 cm. The $CH_4$ and $O_2$ gases are diluted in helium with partial pressures of 0.133, 0.067 and 0.800 atmospheres respectively. The applicator is fed by a microwave generator not shown in the figure. The amplitude of the power emitted is controlled so as to make the temperature of the catalyst, which is measured with a Chromel-Alumel thermocouple 5, constant and kept constant at the desired value. This applicator can also be employed in a more refined laboratory plant, like that described in the publication by J. M. Thiebaut, H. Ammor, G. Roussy, published in the Journal de Chimie Physique, Volume 85(7), pages 799 to 806, in 1988.

In the pilot version, illustrated in FIG. 2, a sintered silica plate 7 has been placed in the oven 6, on which plate the catalyst 8 in accordance with the invention is placed as a layer a few millimeters in thickness. The plate is placed in a vessel which allows the gaseous reactants to be delivered. A diffuser 9 made of teflon or silica ensures a homogeneous distribution of the gas flow over the surface of the catalyst. The bottom of the oven, through which the gases which have reacted leave, consists of a metal grid 10 which reflects the microwaves entering the oven 11. To ensure a homogeneous distribution of the microwaves over the catalyst, the supply of the oven with the stirrer in fashion 12 (Styher) and of the adaptation system, which are provided by the manufacturer of the oven, have been retained.

Among the doped catalysts in accordance with the invention there may be mentioned: $(SmLiO_2)_{0.8}(CaOMgO)_{0.2}$, $(LaLiO_2)_{0.7}(SrOMgO)_{0.3}$, $(NdLiO_2)_{0.8}(CaOMgO)_{0.2}$; $(SmLiO_2)_{0.8}(CaOMgO)_{0.2}$ being preferred.

In fact, $(SmLiO_2)_{0.8}(CaOMgO)_{0.2}$ is a solid consisting of $SmLiO_2$ molecular groups in which calcium and magnesium ions have been dispersed in the form of CaO and MgO. The calcium ions are divalent positive; they exchange and take the place of the trivalent positive samarium ions. The magnesium ions are divalent positive; they replace the monovalent positive lithium ions. These substitutions contribute therefore to the creation in said catalyst of the electrical charge defects and the geometric deformations characterizing the catalysts in accordance with the invention.

Thus, the $SmLiO_2$ catalyst doped with oxides CaO and MgO is an absorber of microwaves, whereas the pure oxides are, in most cases, insulators. The introduction, as indicated by the formula, of 20% by weight of the $SmLiO_2$ catalyst of calcium and magnesium ions into the initial lattice enables the resultant catalyst to obtain a yield and a selectivity that have hitherto never been obtained with catalytic reactions for controlled oxidation of methane using microwaves.

Figure 3:
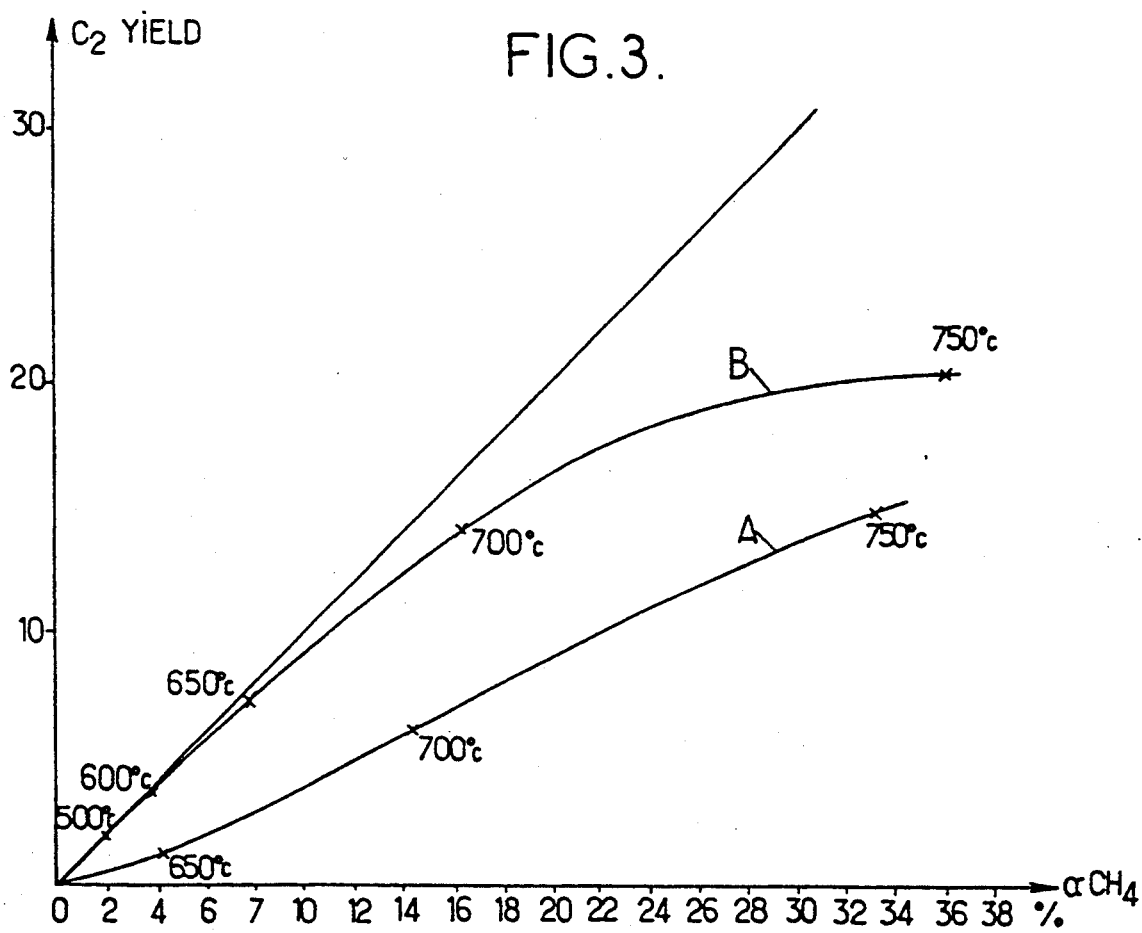
FIG. 3 shows experimental curves indicating the yield of the controlled oxidation reaction of methane as a function of the corresponding degree of progress, in the case of the catalyst in accordance with the invention, heated in a conventional or microwave oven.

The performance of the $(SmLiO_2)_{0.8}(CaOMgO)_{0.2}$ catalyst is illustrated by FIG. 3, in which the yield $\rho$ of the controlled catalytic oxidation of methane using microwaves has been shown as a function of the corresponding degree of progress $\alpha$, the two data being linked by the relationship $\rho = S\alpha$ with S=the selectivity of this same reaction.

According to this illustration the results obtained using the process in accordance with the invention are proportionally better as the corresponding curve approaches the first bisector of the graph, that is to say enables the yield of the reaction to be proportional to its degree of progress with a constant selectivity close to the maximum of 100%.

In a conventional oven most catalysts (including those in accordance with the invention) have operating points which lie on the curve A, that is to say that the yield increases as a function of the degree of progress of the reaction when it is small, and then becomes stabilized when the temperature increases, but always remains much lower than the theoretical yield.

In a microwave oven the catalyst in accordance with the invention has operating points which lie on the curve B, that is to say with a yield approaching the maximum theoretical value (close to the first bisector) in the case of low degrees of progress and departs from it a little when the degree of progress increases.

It has also been possible to compare the results obtained when the catalytic reaction of controlled oxidation of the methane obtained, on the one hand, in a microwave oven and, on the other hand, in a conventional oven with reactors of the same geometry and with identical catalyst temperature and gas pressure conditions.

In the case of the catalyst in accordance with the invention $(SmLiO_2)_{0.8}(CaOMgO)_{0.2}$, it was found:
— that the rate $K_5$ (see reaction scheme above) of the ethylene oxidation reaction is at least ten times lower in the microwave oven than in the conventional oven,
— that the ethane oxidation reaction 4 practically does not take place in the microwave oven, the ratio of the rate constants being very low:

$$K_4^{(\mu)}/K_4^{(cl)} \sim 10^{-4}$$

with $\mu$=microwaves, cl=conventional,
— that the rates $K_1$ and $K_2$ are both multiplied by large factors in the microwave oven when compared with the conventional oven, and that at a temperature of 500° to 600° C. the ratio $K_1/K_2$ is increased by a factor of 10.

Which tends to prove that the use of a catalyst in accordance with the invention in the process in accordance with the invention makes it possible to optimize all the reactions accompanying the controlled oxidation of methane.

In the case of $(LaLiO_2)_{0.67}(SrOMgO)_{0.33}$, the distortion in the catalyst lattice is due to the replacement of lanthanum by strontium.

The selectivity S of this catalyst and the degree of progress $\alpha$ of the reaction of controlled oxidation of methane have been compared in the case where, on the one hand, this catalyst is heated in a microwave oven and, on the other hand, it is heated in a conventional oven in identical reactor geometry, catalyst temperature and gas pressure conditions. The results are summarized in Table I.

TABLE I

|   | Conventional | | | | Microwave | | | |
|---|---|---|---|---|---|---|---|---|
|   | 600° C. | 650° C. | 700° C. | 750° C. | 570° C. | 600° C. | 650° C. | 700° C. |
| $\alpha$ (%) | 2 | 5 | 19 | 30 | 0.5 | 4.0 | 20 | 24 |
| S (%) | 62 | 50 | 50 | 48 | 91.3 | 90 | 72 | 63 |

It appears that the selectivity of the catalyst in accordance with the invention is clearly higher in the case of microwave heating with a degree of progress of the reaction which is also higher.

Among the undoped catalysts in accordance with the invention there may be mentioned $SmLiO_2$, $LaLiO_2$, $LaNaO_2$, $NdNaO_2$ and $SmNaO_2$; $SmLiO_2$ being preferred.

In fact, in the case of $SmLiO_2$ the samarium ion is generally trivalent but, depending on the catalyst preparation, it is possible to obtain 10% of divalent samarium ions. The electrical arrangement of the $O^-$ ions is therefore already a little perturbed and the catalyst therefore exhibits ionic defects in a sufficient number to be used in the process in accordance with the invention, without any actual doping being present.

The same comparison as above was made. The results are summarized in Table II.

TABLE II

|   | Conventional | | | Microwave | | |
|---|---|---|---|---|---|---|
|   | 500° C. | 600° C. | 700° C. | 500° C. | 600° C. | 700° C. |
| $\alpha$ (%) | 5 | 45 | 28 | 4.1 | 26 | 35.5 |
| S (%) | 0.01 | 9 | 55 | 90.5 | 62 | 58 |

It appears that the selectivity of the catalyst in accordance with the invention is clearly higher in the case of microwave heating at temperatures lower than 700° C.

It should, however, be explained that doping of this catalyst with calcium and magnesium oxides improves its performance further.

We claim:
1. A catalytic process for controlled oxidation of methane using microwaves for the synthesis of ethane and ethylene comprising
a) introducing methane over the surface of a catalyst exhibiting in its structure electrical charge defects and geometric deformations enabling it to absorb electromagnetic energy or microwaves, b) subjecting the methane and the catalyst to an electromagnetic field, said catalyst comprising a rare-earth oxide or a rare-earth alkali metal mixed oxide.

2. A process according to claim 1, wherein the catalyst used is doped with at least one alkali metal and/or alkaline-earth metal.

3. A process according to claim 1, wherein the catalyst used is doped with at least one alkali metal and/or alkaline-earth metal which metal is in the form of an oxide.

4. A process according to claim 1, wherein the catalyst used is selected from the group consisting of $SmLiO_2$, $LaLiO_2$, $LaNaO_2$, $NdNaO_2$ and $SmNaO_2$.

5. A process according to claim 1, wherein the catalyst used comprises $SmLiO_2$.

6. A process according to claim 1, wherein the catalyst used is selected from the group consisting of: $(SMLiO_2)_{0.8}(CaOMgO)_{0.2}$, $(LaLi_2)_{0.7}(SrOMgO)_{0.3}$ and $(NdLiO_2)_{0.8}(CaMgO)_{0.2}$.

7. A process according to claim 1, wherein the catalyst used is comprised of $(SMLiO_2)_{0.8}(CaOMgO)_{0.2}$.

8. A process according to claim 1, wherein the electromagnetic field employed comprises microwaves having bands authorized for industrial, scientific and medical applications.

9. A process according to claim 1, wherein the electromagnetic field employed comprises microwaves having bands authorized for industrial, scientific and medical application, for which the frequency is selected from $13560\pm17$ kHz, $27120\pm70$ kHz, $433.92\pm0.80$ MHz, $915\pm15$ MHz, $2450\pm50$ MHz and $5800\pm75$ MHz.

* * * * *